(12) United States Patent
Jeong

(10) Patent No.: US 9,169,309 B2
(45) Date of Patent: Oct. 27, 2015

(54) THERMOSTABLE VARIANTS OF FIBROBLAST GROWTH FACTORS

(75) Inventor: Soon Seog Jeong, Naperville, IL (US)

(73) Assignee: HUMANZYME INC., Chicago, IL (US)

( * ) Notice: Subject to any disclaimer, the term of this patent is extended or adjusted under 35 U.S.C. 154(b) by 0 days.

(21) Appl. No.: 13/408,874

(22) Filed: Feb. 29, 2012

(65) Prior Publication Data

US 2012/0225479 A1  Sep. 6, 2012

Related U.S. Application Data

(60) Provisional application No. 61/448,107, filed on Mar. 1, 2011.

(51) Int. Cl.
| | |
|---|---|
| *A61K 38/18* | (2006.01) |
| *C07K 14/50* | (2006.01) |
| *C12N 5/0789* | (2010.01) |
| *C12N 5/0735* | (2010.01) |

(52) U.S. Cl.
CPC ............ *C07K 14/503* (2013.01); *C12N 5/0606* (2013.01)

(58) Field of Classification Search
CPC ............................ C07K 14/503; C12N 5/0606
See application file for complete search history.

(56) References Cited

U.S. PATENT DOCUMENTS

| | | | | |
|---|---|---|---|---|
| 5,310,883 | A | * | 5/1994 | Seddon et al. ............... 530/399 |
| 5,859,208 | A | | 1/1999 | Fiddes et al. |
| 6,083,706 | A | * | 7/2000 | Florkiewicz et al. .......... 435/7.1 |
| 7,563,769 | B2 | * | 7/2009 | Bogin et al. .................. 514/1.1 |
| 8,372,642 | B2 | * | 2/2013 | Rajesh et al. ................. 435/377 |
| 2009/0111748 | A1 | | 4/2009 | Ellerby et al. |
| 2010/0022453 | A1 | | 1/2010 | Giger et al. |
| 2011/0039793 | A1 | | 2/2011 | Zhang et al. |

FOREIGN PATENT DOCUMENTS

| | | | |
|---|---|---|---|
| EP | 1 444 995 A1 | * | 11/2004 |
| WO | WO 98/37880 | * | 9/1993 |
| WO | WO-03/094835 | | 11/2003 |
| WO | WO 03/094835 | * | 11/2003 |
| WO | WO-2008/038287 A2 | | 4/2008 |
| WO | WO-2010/083051 | | 7/2010 |

OTHER PUBLICATIONS

Levenstein, Mark E. et al., "Basic Fibroblast Growth Factor Support of Human Embryonic Stem Cell Self-Renewal", Stem Cells, (2006), vol. 24, pp. 568-574.

Zakrzewska, Malgorzata et al., "Design of fully active FGF-1 variants with increased stability," Protein Engineering, Design & Selection, (2004), vol. 17, No. 8, pp. 603-611.

Zakrzewska, Malgorzata et al., "Highly Stable Mutants of Human Fibroblast Growth Factor-1 Exhibit Prolonged Biological Action", J. Mol. Biol., (2005), vol. 352, No. 4, pp. 860-875.

* cited by examiner

*Primary Examiner* — Marianne P Allen
(74) *Attorney, Agent, or Firm* — Foley & Lardner LLP

(57) ABSTRACT

The present technology relates to engineered human Fibroblast Growth Factor-2 (FGF2) proteins and methods of using the same. In particular, the methods and compositions relate to FGF2 mutants with increased thermostability compared to the wild-type protein and method for using the proteins in the culturing of embryonic stem cells.

13 Claims, 12 Drawing Sheets

FIGURE 1

| DNA and Amino Acid Sequences of Wild-type and Engineered FGF2 |
|---|
| SEQ ID NO: 1<br>Full-length wild-type FGF2, including propeptide-encoding sequence<br><br>atggcagccgggagcatcaccacgctgcccgccttgcccgaggatggcggcagcggcgccttcccgcccggccacttcaa ggaccccaagcggctgtactgcaaaaacggggggcttcttcctgcgcatccaccccgacggccgagttgacggggtccggga gaagagcgaccctcacatcaagctacaacttcaagcagaagagagaggagttgtgtctatcaaaggagtgtgtgctaaccgtt acctggctatgaaggaagatggaagattactggcttctaaatgtgttacggatgagtgtttcttttttgaacgattggaatctaataa ctacaatacttaccggtcaaggaaatacaccagttggtatgtggcactgaaacgaactgggcagtataaacttggatccaaaac aggacctgggcagaaagctatacttttcttccaatgtctgctaagagctga |
| SEQ ID NO: 2<br>Full-length wild-type FGF2, including propeptide sequence<br><br>1- <u>M A A G S I T T L</u> P A L P E D G G S G A -20<br>21- F P P G H F K D P K R L Y <u>C</u> K N G G F F -40<br>41- L R I H P D G R V D G V R E K S D P H I -60<br>61 K L Q L Q A E E R G V V S I K G V <u>C</u> A N -80<br>81 R Y L A M K E D G R L L A S K <u>C</u> V T D E -100<br>101 <u>C</u> F F F E R L E S N N Y N T Y R S R K Y -120<br>121 T S W Y V A L K R T G Q Y K L G S K T G -140<br>141 P G Q K A I L F L P M S A K S - |
| SEQ ID NO: 3<br>FGF2-encoding DNA excluding propeptide-encoding sequence<br><br>cccgccttgcccgaggatggcggcagcggcgccttcccgcccggccacttcaaggaccccaagcggctgtactgcaaaaa cggggggcttcttcctgcgcatccaccccgacggccgagttgacggggtccgggagaagagcgaccctcacatcaagctaca acttcaagcagaagagagaggagttgtgtctatcaaaggagtgtgtgctaaccgttacctggctatgaaggaagatggaagatt actggcttctaaatgtgttacggatgagtgtttcttttttgaacgattggaatctaataactacaatacttaccggtcaaggaaataca ccagttggtatgtggcactgaaacgaactgggcagtataaacttggatccaaaacaggacctgggcagaaagctatacttttct tccaatgtctgctaagagctga |
| SEQ ID NO: 4<br>FGF2 protein without N-terminal propeptide<br><br>P A L P E D G G S G A F P P G H F K D P K R L Y <u>C</u> K N G G F F<br>L R I H P D G R V D G V R E K S D P H I K L Q L Q A E E R G V<br>V S I K G V <u>C</u> A N R Y L A M K E D G R L L A S K <u>C</u> V T D E <u>C</u><br>F F F E R L E S N N Y N T Y R S R K Y T S W Y V A L K R T G<br>Q Y K L G S K T G P G Q K A I L F L P M S A K S |

Figure 1 (continued)

| DNA and Amino Acid Sequences of Wild-type and Engineered FGF2 |
|---|
| SEQ ID NO: 5<br>FGF2 Q65I + N111G, including propeptide-encoding sequence<br><br>ATGGCAGCCGGGAGCATCACCACGCTGCCCGCCTTGCCCGAGGATGGCGGC<br>AGCGGCGCCTTCCCGCCCGGCCACTTCAAGGACCCCAAGCGGCTGTACTGC<br>AAAAACGGGGGCTTCTTCCTGCGCATCCACCCCGACGGCCGAGTTGACGGG<br>GTCCGGGAGAAGAGCGACCCTCACATCAAGCTACAACTTATAGCAGAAGAG<br>AGAGGAGTTGTGTCTATCAAAGGAGTGTGTGCTAACCGTTACCTGGCTATGA<br>AGGAAGATGGAAGATTACTGGCTTCTAAATGTGTTACGGATGAGTGTTTCTT<br>TTTTGAACGATTGGAATCTAATGGCTACAATACTTACCGGTCAAGGAAATAC<br>ACCAGTTGGTATGTGGCACTGAAACGAACTGGGCAGTATAAACTTGGATCC<br>AAAACAGGACCTGGGCAGAAAGCTATACTTTTTCTTCCAATGTCTGCTAAGA<br>GCTGA |
| SEQ ID NO: 6<br>FGF2 Q65I + N111G, including propeptide sequence<br><br>MAAGSITTLPALPEDGGSGAFPPGHFKDPKRLYCKNGGFFLRIHPDGRVDGVRE<br>KSDPHIKLQLIAEERGVVSIKGVCANRYLAMKEDGRLLASKCVTDECFFFERLE<br>SNGYNTYRSRKYTSWYVALKRTGQYKLGSKTGPGQKAILFLPMSAKS. |
| SEQ ID NO: 7<br>FGF2 Q65I + N111G + C96S, including propeptide-encoding sequence<br><br>ATGGCAGCCGGGAGCATCACCACGCTGCCCGCCTTGCCCGAGGATGGCGGC<br>AGCGGCGCCTTCCCGCCCGGCCACTTCAAGGACCCCAAGCGGCTGTACTGC<br>AAAAACGGGGGCTTCTTCCTGCGCATCCACCCCGACGGCCGAGTTGACGGG<br>GTCCGGGAGAAGAGCGACCCTCACATCAAGCTACAACTTATAGCAGAAGAG<br>AGAGGAGTTGTGTCTATCAAAGGAGTGTGTGCTAACCGTTACCTGGCTATGA<br>AGGAAGATGGAAGATTACTGGCTTCTAAAAGTGTTACGGATGAGTGTTTCTT<br>TTTTGAACGATTGGAATCTAATGGCTACAATACTTACCGGTCAAGGAAATAC<br>ACCAGTTGGTATGTGGCACTGAAACGAACTGGGCAGTATAAACTTGGATCC<br>AAAACAGGACCTGGGCAGAAAGCTATACTTTTTCTTCCAATGTCTGCTAAGA<br>GCTGA |
| SEQ ID NO: 8<br>FGF2 Q65I + N111G + C96S, including propeptide sequence<br><br>MAAGSITTLPALPEDGGSGAFPPGHFKDPKRLYCKNGGFFLRIHPDGRVDGVRE<br>KSDPHIKLQLIAEERGVVSIKGVCANRYLAMKEDGRLLASKSVTDECFFFERLES<br>NGYNTYRSRKYTSWYVALKRTGQYKLGSKTGPGQKAILFLPMSAKS. |
| SEQ ID NO: 9<br>FGF2 Q65I + N111G + C78S + C96S, including propeptide-encoding sequence<br><br>ATGGCAGCCGGGAGCATCACCACGCTGCCCGCCTTGCCCGAGGATGGCGGC<br>AGCGGCGCCTTCCCGCCCGGCCACTTCAAGGACCCCAAGCGGCTGTACTGC<br>AAAAACGGGGGCTTCTTCCTGCGCATCCACCCCGACGGCCGAGTTGACGGG<br>GTCCGGGAGAAGAGCGACCCTCACATCAAGCTACAACTTATAGCAGAAGAG<br>AGAGGAGTTGTGTCTATCAAAGGAGTGAGTGCTAACCGTTACCTGGCTATG |

FIGURE 1 (Continued)

| DNA and Amino Acid Sequences of Wild-type and Engineered FGF2 |
|---|
| AAGGAAGATGGAAGATTACTGGCTTCTAAAAGTGTTACGGATGAGTGTTTCT TTTTTGAACGATTGGAATCTAATGGCTACAATACTTACCGGTCAAGGAAATA CACCAGTTGGTATGTGGCACTGAAACGAACTGGGCAGTATAAACTTGGATC CAAAACAGGACCTGGGCAGAAAGCTATACTTTTTCTTCCAATGTCTGCTAAG AGCTGA |
| SEQ ID NO: 10<br>FGF2 Q65I + N111G + C78S + C96S, including propeptide sequence<br><br>MAAGSITTLPALPEDGGSGAFPPGHFKDPKRLYCKNGGFFLRIHPDGRVDGVRE KSDPHIKLQLIAEERGVVSIKGVSANRYLAMKEDGRLLASKSVTDECFFFERLES NGYNTYRSRKYTSWYVALKRTGQYKLGSKTGPGQKAILFLPMSAKS. |

FIGURE 4

- 1. -QNm
- 2. -QNCm
- 3. -QNCCm

SEQUENCE LISTING

<160> NUMBER OF SEQ ID NOS: 13

<210> SEQ ID NO 1
<211> LENGTH: 468
<212> TYPE: DNA
<213> ORGANISM: Homo sapiens

<400> SEQUENCE: 1

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga gatggaaga ttactggctt ctaaatgtgt tacggatgag      300
tgtttctttt ttgaacgatt ggaatctaat aactacaata cttaccggtc aaggaaatac     360
accagttggt atgtggcact gaaacgaact gggcagtata acttggatc caaaacagga      420
cctgggcaga agctatact ttttcttcca atgtctgcta agagctga                   468
```

<210> SEQ ID NO 2
<211> LENGTH: 155
<212> TYPE: PRT
<213> ORGANISM: Homo sapiens

<400> SEQUENCE: 2

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 3
<211> LENGTH: 441
<212> TYPE: DNA
<213> ORGANISM: Homo sapiens

<400> SEQUENCE: 3

```
cccgccttgc ccgaggatgg cggcagcggc gccttcccgc ccggccactt caaggacccc      60
aagcggctgt actgcaaaaa cgggggcttc ttcctgcgca tccaccccga cggccgagtt     120
gacggggtcc gggagaagag cgaccctcac atcaagctac aacttcaagc agaagagaga     180
ggagttgtgt ctatcaaagg agtgtgtgct aaccgttacc tggctatgaa ggaagatgga     240
```

-continued

```
agattactgg cttctaaatg tgttacggat gagtgtttct tttttgaacg attggaatct    300
aataactaca atacttaccg gtcaaggaaa tacaccagtt ggtatgtggc actgaaacga    360
actgggcagt ataaacttgg atccaaaaca ggacctgggc agaaagctat acttttttctt   420 ccaatgtctg ctaagagctg a                                              441
```

<210> SEQ ID NO 4
<211> LENGTH: 146
<212> TYPE: PRT
<213> ORGANISM: Homo sapiens

<400> SEQUENCE: 4

```
Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145
```

<210> SEQ ID NO 5
<211> LENGTH: 468
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(465)

<400> SEQUENCE: 5

```
atg gca gcc ggg agc atc acc acg ctg ccc gcc ttg ccc gag gat ggc      48
Met Ala Ala Gly Ser Ile Thr Thr Leu Pro Ala Leu Pro Glu Asp Gly
1               5                   10                  15 ggc agc ggc gcc ttc ccg ccc ggc cac ttc aag gac ccc aag cgg ctg      96
Gly Ser Gly Ala Phe Pro Pro Gly His Phe Lys Asp Pro Lys Arg Leu
            20                  25                  30 tac tgc aaa aac ggg ggc ttc ttc ctg cgc atc cac ccc gac ggc cga     144
Tyr Cys Lys Asn Gly Gly Phe Phe Leu Arg Ile His Pro Asp Gly Arg
        35                  40                  45 gtt gac ggg gtc cgg gag aag agc gac cct cac atc aag cta caa ctt    192
Val Asp Gly Val Arg Glu Lys Ser Asp Pro His Ile Lys Leu Gln Leu
    50                  55                  60 ata gca gaa gag aga gga gtt gtg tct atc aaa gga gtg tgt gct aac    240
Ile Ala Glu Glu Arg Gly Val Val Ser Ile Lys Gly Val Cys Ala Asn
```

```
                65                  70                  75                  80
cgt tac ctg gct atg aag gaa gat gga aga tta ctg gct tct aaa tgt       288
Arg Tyr Leu Ala Met Lys Glu Asp Gly Arg Leu Leu Ala Ser Lys Cys
                85                  90                  95 gtt acg gat gag tgt ttc ttt ttt gaa cga ttg gaa tct aat ggc tac       336
Val Thr Asp Glu Cys Phe Phe Phe Glu Arg Leu Glu Ser Asn Gly Tyr
            100                 105                 110 aat act tac cgg tca agg aaa tac acc agt tgg tat gtg gca ctg aaa       384
Asn Thr Tyr Arg Ser Arg Lys Tyr Thr Ser Trp Tyr Val Ala Leu Lys
        115                 120                 125 cga act ggg cag tat aaa ctt gga tcc aaa aca gga cct ggg cag aaa       432
Arg Thr Gly Gln Tyr Lys Leu Gly Ser Lys Thr Gly Pro Gly Gln Lys
    130                 135                 140 gct ata ctt ttt ctt cca atg tct gct aag agc tga                       468
Ala Ile Leu Phe Leu Pro Met Ser Ala Lys Ser
145                 150                 155

<210> SEQ ID NO 6
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Ile Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Gly Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 7
<211> LENGTH: 468
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(465)

<400> SEQUENCE: 7 atg gca gcc ggg agc atc acc acg ctg ccc gcc ttg ccc gag gat ggc        48
Met Ala Ala Gly Ser Ile Thr Thr Leu Pro Ala Leu Pro Glu Asp Gly
```

```
                1               5                      10                      15
ggc agc ggc gcc ttc ccg ccc ggc cac ttc aag gac ccc aag cgg ctg        96
Gly Ser Gly Ala Phe Pro Pro Gly His Phe Lys Asp Pro Lys Arg Leu
                20                      25                      30 tac tgc aaa aac ggg ggc ttc ttc ctg cgc atc cac ccc gac ggc cga        144
Tyr Cys Lys Asn Gly Gly Phe Phe Leu Arg Ile His Pro Asp Gly Arg
            35                      40                      45 gtt gac ggg gtc cgg gag aag agc gac cct cac atc aag cta caa ctt        192
Val Asp Gly Val Arg Glu Lys Ser Asp Pro His Ile Lys Leu Gln Leu
        50                      55                      60 ata gca gaa gag aga gga gtt gtg tct atc aaa gga gtg tgt gct aac        240
Ile Ala Glu Glu Arg Gly Val Val Ser Ile Lys Gly Val Cys Ala Asn
65                      70                      75                      80 cgt tac ctg gct atg aag gaa gat gga aga tta ctg gct tct aaa agt        288
Arg Tyr Leu Ala Met Lys Glu Asp Gly Arg Leu Leu Ala Ser Lys Ser
                85                      90                      95 gtt acg gat gag tgt ttc ttt ttt gaa cga ttg gaa tct aat ggc tac        336
Val Thr Asp Glu Cys Phe Phe Phe Glu Arg Leu Glu Ser Asn Gly Tyr
                100                     105                     110 aat act tac cgg tca agg aaa tac acc agt tgg tat gtg gca ctg aaa        384
Asn Thr Tyr Arg Ser Arg Lys Tyr Thr Ser Trp Tyr Val Ala Leu Lys
            115                     120                     125 cga act ggg cag tat aaa ctt gga tcc aaa aca gga cct ggg cag aaa        432
Arg Thr Gly Gln Tyr Lys Leu Gly Ser Lys Thr Gly Pro Gly Gln Lys
        130                     135                     140 gct ata ctt ttt ctt cca atg tct gct aag agc tga                        468
Ala Ile Leu Phe Leu Pro Met Ser Ala Lys Ser
145                     150                     155

<210> SEQ ID NO 8
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Ile Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Ser
                85                  90                  95

Val Thr Asp Glu Cys Phe Phe Phe Glu Arg Leu Glu Ser Asn Gly Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 9
<211> LENGTH: 468
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(465)

<400> SEQUENCE: 9

```
atg gca gcc ggg agc atc acc acg ctg ccc gcc ttg ccc gag gat ggc      48
Met Ala Ala Gly Ser Ile Thr Thr Leu Pro Ala Leu Pro Glu Asp Gly
1               5                   10                  15 ggc agc ggc gcc ttc ccg ccc ggc cac ttc aag gac ccc aag cgg ctg      96
Gly Ser Gly Ala Phe Pro Pro Gly His Phe Lys Asp Pro Lys Arg Leu
            20                  25                  30 tac tgc aaa aac ggg ggc ttc ttc ctg cgc atc cac ccc gac ggc cga     144
Tyr Cys Lys Asn Gly Gly Phe Phe Leu Arg Ile His Pro Asp Gly Arg
        35                  40                  45 gtt gac ggg gtc cgg gag aag agc gac cct cac atc aag cta caa ctt     192
Val Asp Gly Val Arg Glu Lys Ser Asp Pro His Ile Lys Leu Gln Leu
    50                  55                  60 ata gca gaa gag aga gga gtt gtg tct atc aaa gga gtg agt gct aac     240
Ile Ala Glu Glu Arg Gly Val Val Ser Ile Lys Gly Val Ser Ala Asn
65                  70                  75                  80 cgt tac ctg gct atg aag gaa gat gga aga tta ctg gct tct aaa agt     288
Arg Tyr Leu Ala Met Lys Glu Asp Gly Arg Leu Leu Ala Ser Lys Ser
                85                  90                  95 gtt acg gat gag tgt ttc ttt ttt gaa cga ttg gaa tct aat ggc tac     336
Val Thr Asp Glu Cys Phe Phe Phe Glu Arg Leu Glu Ser Asn Gly Tyr
            100                 105                 110 aat act tac cgg tca agg aaa tac acc agt tgg tat gtg gca ctg aaa     384
Asn Thr Tyr Arg Ser Arg Lys Tyr Thr Ser Trp Tyr Val Ala Leu Lys
        115                 120                 125 cga act ggg cag tat aaa ctt gga tcc aaa aca gga cct ggg cag aaa     432
Arg Thr Gly Gln Tyr Lys Leu Gly Ser Lys Thr Gly Pro Gly Gln Lys
    130                 135                 140 gct ata ctt ttt ctt cca atg tct gct aag agc tga                     468
Ala Ile Leu Phe Leu Pro Met Ser Ala Lys Ser
145                 150                 155
```

<210> SEQ ID NO 10
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Ile Ala Glu Glu Arg Gly Val Val Ser Ile Lys Gly Val Ser Ala Asn
65                  70                  75                  80
```

```
Arg Tyr Leu Ala Met Lys Glu Asp Gly Arg Leu Leu Ala Ser Lys Ser
                85                  90                  95

Val Thr Asp Glu Cys Phe Phe Phe Glu Arg Leu Glu Ser Asn Gly Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 11
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: Gln, Leu, Ile or Val
<220> FEATURE:
<221> NAME/KEY: MOD_RES
<222> LOCATION: (96)..(96)
<223> OTHER INFORMATION: Cys, Ser or Thr
<220> FEATURE:
<221> NAME/KEY: MOD_RES
<222> LOCATION: (111)..(111)
<223> OTHER INFORMATION: Asn, Ala or Gly

<400> SEQUENCE: 11

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Xaa Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Xaa
                85                  90                  95

Val Thr Asp Glu Cys Phe Phe Phe Glu Arg Leu Glu Ser Asn Xaa Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 12
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Ile Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Ser Val Thr Asp Glu Cys Phe Phe Phe Glu
                85                  90                  95

Arg Leu Glu Ser Asn Gly Tyr Asn Thr Tyr Arg Ser Arg Lys Tyr Thr
                100                 105                 110

Ser Trp Tyr Val Ala Leu Lys Arg Thr Gly Gln Tyr Lys Leu Gly Ser
            115                 120                 125

Lys Thr Gly Pro Gly Gln Lys Ala Ile Leu Phe Leu Pro Met Ser Ala
130                 135                 140

Lys Ser
145

<210> SEQ ID NO 13
<211> LENGTH: 155
<212> TYPE: PRT
<213> ORGANISM: Homo sapiens

<400> SEQUENCE: 13

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155
```

THERMOSTABLE VARIANTS OF FIBROBLAST GROWTH FACTORS

RELATED APPLICATIONS

This application claims the benefit of U.S. Provisional Application 61/448,107, filed Mar. 1, 2011, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Apr. 18, 2012, is named 92496121.txt and is 20,706 bytes in size.

FIELD OF THE INVENTION

The present technology relates to engineered Fibroblast Growth Factor-2 (FGF2) with increased thermostability, and uses of same for the culturing of embryonic stem cells.

BACKGROUND

Human embryonic stem cells are typically cultured in media that contains basic fibroblast growth factor proteins. The growth factors are usually supplied in the form of fibroblast feeder layers or by the use of fibroblast-conditioned media. Supplementing such media with recombinant growth factors and cytokines helps boost self-renewal and differentiation of both embryonic and induced pluripotent stem cells.

In this regard, Fibroblast Growth Factor-2 (FGF2) is an important component of human embryonic stem cell culture media because it helps maintain the cells in an undifferentiated state. Thus, one function of FGF2 is to prolong the pluripotency period of the cells and, consequently, their ability to differentiate into various different cell types. See Xu C, et al. (2005) *Stem Cells* 23:315-323. Sufficiently high concentrations of FGF2 permit the culture of human embryonic stem cells in fibroblast unconditioned medium, which does not contain fibroblasts. See Levenstein M E, et al. (2006) *Stem Cells* 24:568-574.

FGF2 is however more rapidly degraded in fibroblast unconditioned medium than in fibroblast-conditioned medium when incubated with embryonic stem cells for prolonged periods at 37° C. See Levenstein M E, et al. (2006) *Stem Cells* 24:568-574. Consequently, it is usually necessary to supplement the unconditioned medium with fresh FGF2 on a daily basis, in order to maintain an effective concentration in the culture. The short half-life of FGF2 in culture is of concern in the industry from a cost perspective, especially in the context of manufacturing schemes that employ large-scale cell cultures to produce stem cell-based therapeutics.

SUMMARY

The present disclosure generally provides compositions and methods for the culture of embryonic stem ("ES") cells. Specifically, the disclosure provides FGF2 variants with increased thermostability compared to wild-type FGF2.

In some embodiments, the composition comprises an isolated polynucleotide encoding a polypeptide selected from the group consisting of: (i) a variant of SEQ ID NO:2, or a fragment thereof, comprising at least one amino acid substitution selected from the group consisting of Q65L, Q65I, Q65V, N111A, N111G, C96S, and C96T; and (ii) a polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. In some embodiments, the polypeptide encoded comprises amino acid substitutions Q65I, N111G, and C96S. In some embodiments, the isolated polynucleotide of claim 1, wherein the polypeptide encoded comprises SEQ ID NO:8.

In another aspect, the disclosure provides an expression vector comprising an isolated polynucleotide encoding a polypeptide selected from the group consisting of: (i) a variant of SEQ ID NO:2, or a fragment thereof, comprising at least one amino acid substitution selected from the group consisting of Q65L, Q65I, Q65V, N111A, N111G, C96S, and C96T; and (ii) a polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. In some embodiments, the polypeptide encoded comprises amino acid substitutions Q65I, N111G, and C96S. In some embodiments, the expression vector comprises a polynucleotide encoding the polypeptide of SEQ ID NO:8.

In another aspect, the disclosure provides an isolated polypeptide selected from the group consisting of (i) a variant of SEQ ID NO:2, or a fragment thereof, comprising at least one amino acid substitution selected from the group consisting of Q65L, Q65I, Q65V, N111A, N111G, C96S, and C96T; and (ii) a polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. In some embodiments, the polypeptide comprises amino acid substitutions Q65I, N111G, and C96S. In some embodiments, the polypeptide comprises SEQ ID NO: 8.

In another aspect, the present disclosure provides a method for culturing embryonic stem cells comprising culturing the embryonic stem cells in a feeder-independent culture medium comprising an effective amount of the polypeptide of claim 6, wherein the effective amount comprises the amount necessary to maintain the cells with an undifferentiated morphology for at least 5 passages. In some embodiments, the feeder-independent medium is hESF9, mTeSR1, or STEMPRO®. In some embodiments, the effective amount polypeptide is about 1.0 ng/µl to about 100 ng/µl of culture medium. In some embodiments, the embryonic stems cells are human ES cells, mouse ES cells, bovine ES cells, or feline ES cells.

In another aspect, the present disclosure provides a method for maintaining human embryonic stem cells in an undifferentiated state comprising contacting human embryonic stem cells with an effective amount of a polypeptide comprising SEQ ID NO:8 or a variant of SEQ ID NO:4 comprising amino acid substitutions Q56I, N102G, and C87S. In some embodiments, the effective amount of polypeptide is about 1.0 ng/µl to about 100 ng/µl of culture medium.

BRIEF DESCRIPTION OF THE DRAWINGS

FIG. 1: Human FGF2 (FGF-basic). The N-terminal propeptide is underlined, followed by 146 amino acid mature secreted peptide. Four cysteines are shown in bold underline.

Figure 4:
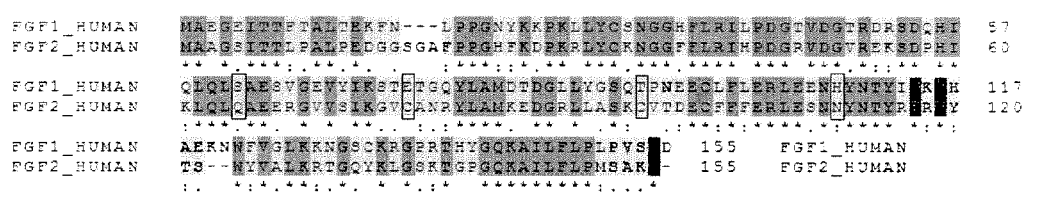

FIG. 4: Pair wise sequence alignment of human FGF1 (SEQ ID NO: 13) and FGF2 (SEQ ID NO: 2). Four engineering target residues are black boxed.

DETAILED DESCRIPTION

General

Figure 2:
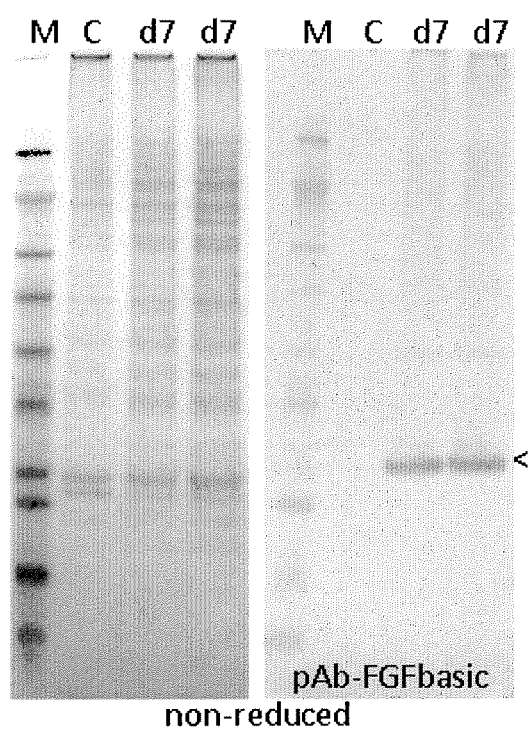
FIG. 2: SDS-PAGE Coomassie stain and Western blot of wild-type FGF2 expression in human cells.
Figure 3:
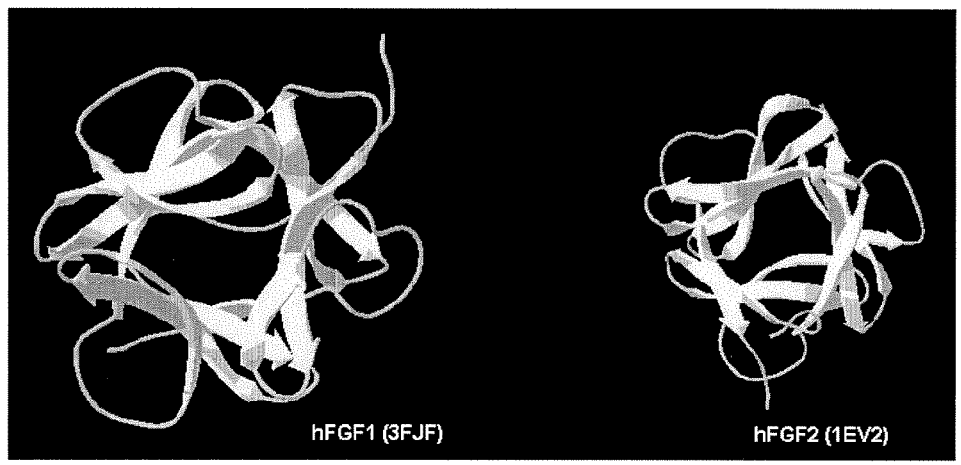
FIG. 3: X-ray crystal structures of human FGF1 (3FJF; left) and FGF2 (1EV2; right) that have a common structure.
Figure 5:
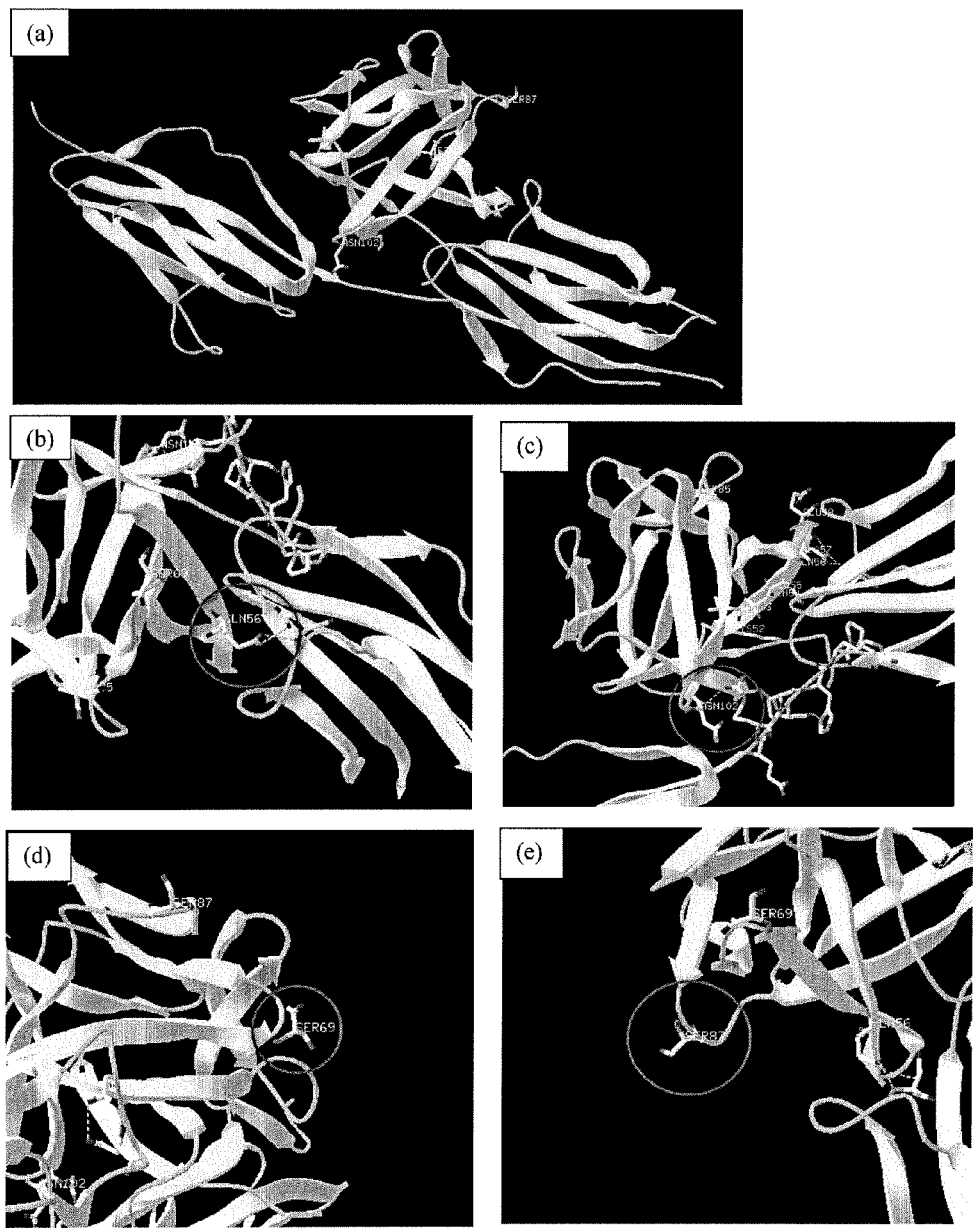
FIGS. 5(a)-(e): (a) X-ray crystal structure of human FGF2 bound to its receptor. All four cysteines were mutated to serines to improve solubility. Locations of engineering target residues are (b) Q65, (c) N111, (d) C78, and (e) C96.

It is to be appreciated that certain aspects, modes, embodiments, variations and features of the invention are described below in various levels of detail in order to provide a substantial understanding of the present invention.

The present disclosure relates to engineered FGF2 molecules with increased thermostability compared to the wild-type protein. The engineered molecules have a longer half-life in human cell culture than the wild-type protein, and are more conducive to large scale production of the recombinant proteins in human cells.

The details of one or more embodiments of the invention are set forth in the accompanying description below. Although any methods and materials similar or equivalent to those described herein can be used in the practice or testing of the present invention, suitable methods and materials are now described. Other features, objects, and advantages of the invention will be apparent from the description and the claims. Generally, enzymatic reactions and purification steps are performed according to the manufacturer's specifications.

The techniques and procedures described herein are generally performed according to conventional methods in the art and various general references, which are provided throughout this document. See generally, *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively. Generally, the nomenclature used herein and the laboratory procedures in cell culture, molecular genetics, organic chemistry, analytical chemistry and nucleic acid chemistry and hybridization described below are those well known and commonly employed in the art. Standard techniques are used for nucleic acid and peptide synthesis. Standard techniques, or modifications thereof, are used for chemical syntheses and chemical analyses. All references cited herein are incorporated herein by reference in their entireties and for all purposes to the same extent as if each individual publication, patent, or patent application was specifically and individually incorporated by reference in its entirety for all purposes.

DEFINITIONS

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term that are not clear to persons of ordinary skill in the art, given the context in which it is used, "about" will mean up to plus or minus 10% of the particular term.

As used herein, "FGF2" refers to human Fibroblast Growth Factor-2. Human FGF2 is a 16 kDa protein with a length of 146 amino acids. See FIG. 1 and SEQ ID NOs 1 and 2. Although the growth factor contains four cysteine residues that are highly conserved among different species, the residues do not form intramolecular disulfide bonds that contribute the structural stability of the protein. FGF2 is unusual among growth factors in that the protein is not glycosylated and it is not secreted via the conventional ER/Golgi pathway. See, for instance, Engling A, et al. (2002) *J Cell Sci* 115:3619-3631.

As used herein, "expression vector" refers to plasmid or circular DNA capable of directing expression of a polynucleotide under the direction of an operable promoter. The vector may be optimized to express in a variety of cell systems, including but not limited to bacterial cells, mammalian cells, human cells, insect cells, or plant cells. Likewise, the vector may be optimized for cell-free expression of the polynucleotide using methods known in the art. The vector may comprise any operable promoter, enhancer, intron, or other sequence relevant to the production of recombinant protein as compatible with the particular cell system in use. In some embodiments, the vector comprises a human CMV immediate early enhancer. In some embodiments, the vector comprises a human beta-actin promoter. In some embodiments, the vector comprises a human beta-globin intron. In some embodiments, the vector comprises an antibiotic resistance marker gene.

As used herein, a "fragment" of FGF2 or an engineered FGF2 protein refers to a portion of the patent amino acid sequence, wherein the portion comprises contiguous amino acids and possesses at least partial FGF2 activity. A "fragment" of the engineered FGF2 variants described herein will also demonstrate increased thermostability compared to the corresponding fragment of the wild-type FGF2 protein. In some embodiments, the fragment comprises at least about 10, at least about 15, at least about 20, at least about 25, at least about 30, at least about 35, at least about 40, at least about 45, at least about 50, at least about 55, at least about 60, at least about 65, at least about 70, at least about 75 at least about 80, at least about 85, at least about 90, at least about 95, at least about 100, at least about 105, at least about 110, at least about 115, at least about 120, at least about 125, at least about 130, at least about 135, at least about 140, at least about 145 contiguous amino acids. In some embodiments, the present disclosure provides an isolated polynucleotide encoding a variant fragment of SEQ ID NO:2 comprising at least one amino acid substitution selected from the group consisting of Q65L, Q65I, Q65V, N111A, N111G, C96S, and C96T. In some embodiments, the present disclosure provides a polynucleotide encoding a polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. In some embodiments, the present disclosure provides an isolated polypeptide comprising a variant of SEQ ID NO:2, or a fragment thereof, comprising at least one amino acid substitution selected from the group consisting of Q65L, Q65I, Q65V, N111A, N111G, C96S, and C96T. In some embodiments, the present disclosure provides an isolated polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. As used herein, the term "variant" is synonymous with "mutant" and refers to a polynucleotide or polypeptide sequence that has a different nucleic acid or amino acid sequence as compared to the wild-type sequence. Exemplary differences can include, without limitation, substitutions, deletions, insertions and inversions. The number of nucleotides or amino acids may vary; e.g., in some embodiments, a polypeptide variant includes one, two, three, four or more amino acid substitutions. In some embodiments, a variant of SEQ ID NO: 2, or a fragment of SEQ ID NO: 2 includes the one or more of the following amino acid substitutions: Q65L, Q65I, Q65V, N111A, N111G, C96S, and C96T. In some embodiments, a variant of SEQ ID NO: 2, or a fragment of SEQ ID NO: 2 includes the following amino acid substitutions Q65I, N111G, and C96S. In some embodiments, a variant of SEQ ID NO:4 includes the following amino acid substitutions: Q56I, N102G, and C87S.

As used herein, "embryonic stem (ES) cells" refers to pluripotent stem cells derived from the inner cell mass of the blastocyst, an early-stage embryo. By definition, ES cells have the capacity to differentiate into all derivatives of the three primary germ layers: ectoderm, endoderm, and mesoderm. In some embodiments, the ES cells are human ES cells. In some embodiments, the ES cells are bovine ES cells. In some embodiments, the ES cells are mouse ES cells. In some embodiments, the ES cells are feline ES cells. As used herein, "stem cells" refers generally to any self-renewing cell type including naturally pluripotent or multipotent cells, and induced pluripotent or multipotent cells. Examples of stem cells amenable to the present methods include but are not limited to embryonic stem cells, adult stem cells, and tissue-specific stem cells. Accordingly, the present methods may be practiced using any stem cell requiring, or which can utilize, FGF2 supplementation in culture for growth or improved growth. In some embodiments, the stem cells are embryonic stem cells. In some embodiments, the stem cells adult stem cells. In some embodiments, the stem cells are tissue-specific stem cells. In some embodiments, the stem cells are naturally pluripotent or multipotent. In some embodiments, the pluripotency or multipotency of the cells is induced.

As used herein, "effective amount" refers to the amount required to achieve a desired effect. For example, the desired effect may be to maintain ES cells in an undifferentiated state. One of skill in the art will understand that what constitutes an effective amount will vary with the specific conditions used and outcome desired. In some embodiments, an effective amount is from about 0.20 ng/µl to about 500 ng/µl of FGF2 or FGF2 variant. In some embodiments, the effective amount is 0.25 ng/µl of FGF2 or FGF2 variant. In some embodiments, an effective amount is 1.0 In some embodiments, the to 100 ng/µl of FGF2 or FGF2 variant.

As used herein, maintaining stem cells in an "undifferentiated morphology" or "undifferentiated state" refers to maintaining the cells in a pluripotent or multipotent state. Pluripotency or multipotency of cells can be assessed using methods known in the art, including nut not limited to, pluripotency markers such as the mCherry Nanog reporter gene. Additionally or alternatively, pluripotency may assessed by the general morphology of the cells according to what is known in the art about the particular cell type in use.

Compositions

The present disclosure relates to engineered FGF2 molecules with increased thermostability compared to the wild-type protein. The disclosure provides a characterization of the engineered molecules, a demonstration of the effect of the engineered mutations on the thermostability of the protein, and methods for using the proteins in the culture of embryonic stem (ES) cells.

Because FGF2 is naturally expressed at very low levels it is very difficult to isolate significant quantities from animal tissues. Therefore, most commercially available FGF2 is a recombinant protein expressed in *E. coli*, which typically yields approximately 1-10 mg of FGF2 per liter *E. coli* cell culture. However, FGF2 expressed in *E. coli* and other bacterial systems localizes to inclusion bodies, requiring renaturation of the protein after purification. See Gasparian M E, et al. (2009) *Biochemistry (Moscow)* 74:221-225. The solubility and activity of *E. coli*-expressed FGF2 is however improved by substituting the cysteine residues at positions 78 and 96 with serine residues, which does not compromise the structural stability of the protein. See Wang J, et al. (2006) *J Biotechnol* 121:442-447. In Chinese Hamster Ovary (CHO) cells, recombinantly expressed FGF2 is secreted as a soluble protein, and is in an appropriate conformation to allow it to be translocated to the cell membrane.

The present disclosure describes mutant FGF2 proteins with increased thermostability compared to the wild-type protein and methods of using the same in the culture of embryonic stem (ES) cells. A related application, PCT/US2009/036975, describing a system for the recombinant production of authentic human proteins, is incorporated herein by reference.

It was discovered during the course of experiments described herein that existing human cell expression systems for the production of recombinant human FGF2 generate yields on the order of a few mg per liter of cell culture. The poor yield appears be a result of the thermo-instability of FGF2 at temperatures optimal for culturing human cells in serum-free media (37° C.). The present technology encompasses novel thermostable mutants of FGF2 that remain biologically active at such temperatures, permitting high yields when expressed in human cells and a prolonged half-life in the culture of human cells compared to the wild-type protein.

Human FGF2 shares more than 90% amino acid sequence identity with other mammalian FGF2 proteins. To identify target residues for improving its thermostability, multiple sequence alignments of human fibroblast growth factor members were studied using the Clustral algorithm. The analysis identified a number of conserved regions in fibroblast growth factor amino acid sequences that are potential targets for directed mutagenesis.

FGF2 was sub-grouped with FGF1, FGF4, FGF5, and FGF6 according to similarity in protein sequence and identity. As disclosed herein, a comparison of the known X-ray crystal structures of FGF2 and human acidic fibroblast growth factor-1 (FGF1) was performed because of similarities in the sequence and subcellular trafficking of the proteins. Both FGF1 and FGF2 have an N-terminal propeptide and are secreted by unconventional pathways. Also, as shown in FIG. 2, the proteins have similar crystal structures. By contrast, FGF4, FGF5, and FGF6 have signal peptides and are conventionally secreted.

Zakrzewska, et al. reported the recombinant expression of stable FGF1 mutants that show increased half-life, strong resistance to proteolysis and enhanced mitogenic activity. Zakrzewska M, et al. (2005) *J Mol Biol* 352:860-875. One such FGF1 mutant, Q55P/S62I/H108G, was thermostable and was less susceptible to protease degradation than the wild-type protein.

To identify the FGF2 amino acids corresponding to FGF1 Q55, S62, and H108, an amino acid sequence alignment between the two proteins was performed using Clustral W. The corresponding residues in FGF2 were identified as: proline 58, glutamine 65, and asparagine 111. In the FGF2 protein sequence, position 58 naturally is a proline, such that it was not necessary to engineer a mutation at this site.

The present disclosure relates to an engineered FGF2 with amino acid substitutions at the following positions: Q65, N111, C78, and C96. According to the FGF2 crystal structure (1EV2), these residues are located on the surface of the protein. Three engineered versions of FGF2 were generated and tested for increased thermostability compared to the wild-type protein: 1) the combination of Q65 (polar) to aliphatic hydrophobic residues (L, I, V) and of N111 to small size residues (A, G); 2) the combination (1) plus C96 to more polar residues (S, T) because FGF1 has threonine for the cysteine in FGF2; and 3) the combination (1) plus C78 and C96 to more polar residues (S, T).

It is within the purview of the geneticist to design and create polynucleotides that encode point mutations, or mutations that result in the expression of a different amino acid than in the non-engineered protein. In this regard, canonical, or "standard," amino acids refer to twenty naturally occurring amino acids encoded by sixty-four triplet codons. All but three of those codons encode "sense" amino acids, whilst the three "nonsense" codons signify stop or termination signals. These 20 amino acids can be split into those that have neutral charges, positive charges, and negative charges:

The "neutral" amino acids are shown below along with their respective three-letter and single-letter code, polarity, and triplet-encoding DNA codons:

Alanine: (Ala, A) nonpolar, neutral (GCT, GCC, GCA, GCG);
Asparagine: (Asn, N) polar, neutral (AAT, AAC);
Cysteine: (Cys, C) nonpolar, neutral (TGT, TGC);
Glutamine: (Gln, Q) polar, neutral (CAA, CAG);
Glycine: (Gly, G) nonpolar, neutral (GGT, GGC, GGA, GGG);
Isoleucine: (Ile, I) nonpolar, neutral (ATT, ATC, ATA);
Leucine: (Leu, L) nonpolar, neutral (TTA, TTG, CTT, CTC, CTA, CTG);
Methionine: (Met, M) nonpolar, neutral (ATG);
Phenylalanine: (Phe, F) nonpolar, neutral (TTT, TTC);
Proline: (Pro, P) nonpolar, neutral (CCT, CCC, CCA, CCG);
Serine: (Ser, S) polar, neutral (TCT, TCC, TCA, TCG, AGT, AGC);
Threonine: (Thr, T) polar, neutral (ACT, ACC, ACA, ACG);
Tryptophan: (Trp, W) nonpolar, neutral (TGG);
Tyrosine: (Tyr, Y) polar, neutral (TAT, TAC);
Valine: (Val, V) nonpolar, neutral (GTT, GTC, GTA, GTG); and
Histidine: (His, H) polar, positive (10%) neutral (90%) (CAT, CAC).

The "positively" charged amino acids are:
Arginine: (Arg, R) polar, positive (CGT, CGC, CGA, CGG, AGA, AGG); and
Lysine: (Lys, K) polar, positive (AAA, AAG).

The "negatively" charged amino acids are:
Aspartic acid: (Asp, D) polar, negative (GAT, GAC); and
Glutamic acid: (Glu, E) polar, negative (GAA, GAG).

Accordingly, the triplets that encode these neutral, positively-, and negatively-charged amino acids can be engineered into an FGF2-encoding polynucleotide as disclosed herein u to create novel thermostable FGF2 mutants.

Thus, in the context of the three illustrative groups of mutations disclosed above, i.e., (1) Q65I+N111G, (2) Q65I+N111G+C96S, and (3) Q65I+N111G+C78S+C96S, it is possible to create the appropriate triplet codon in the larger encoding polynucleotide that effectuates the desired substitution of the chosen amino acid. For instance, at position 65, one of skill in the art could readily change a glutamine (Q) codon (CAA or CAG) to an isoleucine (I) codon (ATT, ATC, or ATA) by making the appropriate nucleotide changes in the coding sequence. Accordingly, one of skill in the art could readily make the aforementioned mutations and amino acid substitutions. The present technology is not limited, however, to just these particular combinations of FGF2 amino acid substitutions. Any other point mutation can be effected in an FGF2 coding sequence to create other amino acid substitutions to create other FGF2 mutants.

In this regard, the engineered plasmid, which contains the mutated FGF2 polynucleotide coding sequence can be easily transfected into human cells and expressed either in cells that are, or are not, adapted to growth in serum-free suspension culture. See, for instance, the methods and materials described in PCT/US2009/036975, which is incorporated herein by reference. In one embodiment, FGF2-expressing human cells can be cultured in serum-free media for 7 days before harvesting for purification. Methods for purifying proteins from cell culture are well known, such as by using appropriately equilibrated DEAE columns onto which various fractions of the culture are loaded and subsequently eluted. The expression level of the recombinant FGF2 mutant protein can be readily analyzed, such as by SDS-PAGE Coomassie staining and Western blotting. As elaborated upon in the Examples below, the combination of Q65I+N111G+C96S (QNCm) mutations unexpectedly increased the expression level of the protein compared to the wild-type protein and the other engineered proteins. This outcome was unexpected because the stability of authentic FGF2 from human cell expression was not improved either by introducing Q65I+N111G (QNm) in addition to existing P58 as of mimicking FGF1 engineering, or by substituting both cysteines with serines, Q65I+N111G+C78S+C96S (QNCCm), as of *E. coli* expressed protein.

To test the thermostability of a recombinantly expressed FGF2 mutant, one method may entail storing *E. coli*-expressed wild-type FGF2 and human cell-expressed FGF2 mutants at minus-80° C., at 37° C., and at 37° C. for various periods of time in serum-free culture medium. Afterwards, the FGF2 proteins can be assayed for their stability by monitoring their ability to stimulate 3T3 cell proliferation. See the Examples below on exemplary methods and materials for performing a 3T3 cell proliferation stability assay.

The assay results revealed that the Q65I+N111G+C96S FGF2 mutant retained the same bioactivity no matter which temperature and time period it was stored. By contrast, the wild-type FGF2 lost half of its activity when stored at 37° C. for 2 hours and lost 90% of its activity after 24 hours at 37° C. The Q65I+N111G+C96S FGF2 mutant had a 10-fold improvement in thermostability in repeated cell based assays.

In some embodiments, the present compositions comprise full-length FGF2 bearing amino acid substitutions that increase its thermostability compared to the wild-type protein. Amino acid substitutions may be introduced into a protein through molecular biology techniques known in the art, such as by PCR-mediated mutagenesis. Recombinant proteins bay be expressed in a variety of cell systems, including but not limited to bacterial and mammalian systems, using expression vectors and culture conditions appropriate to the cell type. Recombinant proteins expressed in these cells can be purified and characterized according to methods known in the art.

In some embodiments, the present compositions comprise full-length FGF2 bearing at least on amino acid substitution. In some embodiments, the substitutions are selected from the group consisting of Q65L, Q65I, Q65V, N111A, N111G, C96S, and C96T.

In some embodiments, the composition comprises a polynucleotide encoding the polypeptide of variant of SEQ ID NO:2, or a fragment thereof, comprising at least one amino acid substitution selected from the group consisting of Q65L, Q65I, Q65V, N111A, N111G, C96S, and C96T. In some embodiments, the composition comprises a polynucleotide encoding a polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. In some embodiments, the polypeptide encoded comprises amino acid substitutions Q65I, N111G, and C96S. In some embodiments, the polypeptide encoded comprises SEQ ID NO:8.

In some embodiments, the present compositions comprise an expression vector comprising a polynucleotide encoding an engineered FGF2 protein. In some embodiments, the vector comprises a polynucleotide encoding the polypeptide variant of SEQ ID NO:2, or a fragment thereof, comprising at least one amino acid substitution selected from the group consisting of Q65L, Q65I, Q65V, N111A, N111G, C96S, and C96T. In some embodiments, the vector comprises a polynucleotide encoding a polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. In some embodiments, the polypeptide expressed from the vector comprises amino acid substitutions Q65I, N111G, and C96S. In some embodiments, the polypeptide encoded comprises SEQ ID NO:8.

In some embodiments, the composition comprises the polypeptide variant of SEQ ID NO:2, or a fragment thereof, comprising at least one amino acid substitution selected from the group consisting of Q65L, Q65I, Q65V, N111A, N111G, C96S, and C96T. In some embodiments, the composition comprises a polypeptide having at least 85% sequence identity to SEQ ID NO:2, or a fragment thereof, comprising at least one amino acid substitution selected from the group consisting of Q65L, Q65I, Q65V, N111A, N111G, C96S, and C96T. In some embodiments, the polypeptide comprises amino acid substitutions Q65I, N111G, and C96S. In some embodiments, the polypeptide comprises SEQ ID NO: 8.

Methods

The present disclosure provides methods for using engineered FGF2 proteins with increased thermostability compared to the wild-type protein in the culture of ES cells. The superior thermostability and bioactivity of the Q65I+N111G+C96S FGF2 mutant translates to a prolonged period of pluripotency of human embryonic stem cells in an undifferentiated state, compared to ES cells exposed to wild-type FGF2.

The results disclosed herein show significantly more differentiation in cultures supplemented with wild-type FGF2 than with the 65I+N111G+C96S substituted FGF2 added to a feeder-independent culture. Therefore, stem cell culture with the Q65I+N111G+C96S FGF2 requires less FGF2 supplementation that cultures supplemented with the wild-type protein, which provides a cost savings. In addition, use of the substituted FGF2 reduces the potential for inadvertent contamination of cell cultures by reducing the need for human handling and manipulation of the cultures. The commercial value of the illustrative Q65I+N111G+C96S FGF2 mutant is readily apparent in terms of requiring less FGF2 protein and handling and human intervention during the culturing process, which translates to reductions in labor, costs, and time.

Accordingly, the present inventive technology encompasses methods of using thermostable FGF2 mutants, such as the Q65I+N111G+C96S FGF2, in cell culture and for maintaining human embryonic stem cells in an undifferentiated state. In some embodiments, the methods comprise culturing the embryonic stem cells in a feeder-independent culture medium comprising an effective amount of the polypeptide of claim 6, wherein the effective amount comprises the amount necessary to maintain the cells with an undifferentiated morphology for at least 5 passages. In some embodiments, the feeder-independent medium is hESF9, mTeSR1, or STEMPRO®. In some embodiments, the effective amount polypeptide is about 1.0 ng/µl to about 100 ng/µl of culture medium. In some embodiments, the embryonic stems cells are human ES cells, mouse ES cells, bovine ES cells, or feline ES cells.

The present disclosure also provides methods for maintaining human embryonic stem cells in an undifferentiated state comprising contacting human embryonic stem cells with a an effective amount of a polypeptide comprising SEQ ID NO:8 or SEQ ID NO:4 comprising amino acid substitutions Q56I, N102G, and C87S. In some embodiments, the effective amount polypeptide is about 1.0 ng/µl to about 100 ng/µl of culture medium.

EXAMPLES

The following examples are presented in order to more fully illustrate the embodiments of the present technology. These examples should in no way be construed as limiting the scope of the invention, as defined by the appended claims.

Example 1

Human Cell Expression

Three engineered human FGF2 genes were generated and cloned into the HumanZyme pHZhag vector, which comprises a human CMV immediate early enhancer, a human beta-actin promoter, and a human beta-globin intron. The three engineered sequences are as follows, with amino acid substitutions shown in bold underline:

(1) FGF2-QNm: Q65I, N111G
atggcagccgggagcatcaccacgctgcccgccttgcccgaggatggcggcagcggcgcc
 M  A  A  G  S  I  T  T  L  P  A  L  P  E  D  G  G  S  G  A ttcccgcccggccacttcaaggaccccaagcggctgtactgcaaaaacgggggcttcttc
 F  P  P  G  H  F  K  D  P  K  R  L  Y  C  K  N  G  G  F  F ctgcgcatccaccccgacggccgagttgacggggtccgggagaagagcgaccctcacatc
 L  R  I  H  P  D  G  R  V  D  G  V  R  E  K  S  D  P  H  I aagctacaacttatagcagaagagagaggagttgtgtctatcaaggagtgtgtgctaac
 K  L  Q  L  I  A  E  E  R  G  V  V  S  I  K  G  V  C  A  N cgttacctggctatgaaggaagatggaagattactggcttctaaatgtgttacggatgag
 R  Y  L  A  M  K  E  D  G  R  L  L  A  S  K  C  V  T  D  E tgtttctttttgaacgattggaatctaatggctacaatacttaccggtcaaggaaatac
 C  F  F  F  E  R  L  E  S  N  G  Y  N  T  Y  R  S  R  K  Y accagttggtatgtggcactgaaacgaactgggcagtataaacttggatccaaaacagga
 T  S  W  Y  V  A  L  K  R  T  G  Q  Y  K  L  G  S  K  T  G Cctgggcagaaagctatacttttcttccaatgtctgctaagagctga (SEQ ID NO: 5)
 P  G  Q  K  A  I  L  F  L  P  M  S  A  K  S  - (SEQ ID NO: 6)

(2) FGF2-QNCm: Q65I, N111G, C96S
atggcagccgggagcatcaccacgctgcccgccttgcccgaggatggcggcagcggcgcc
 M  A  A  G  S  I  T  T  L  P  A  L  P  E  D  G  G  S  G  A ttcccgcccggccacttcaaggaccccaagcggctgtactgcaaaaacgggggcttcttc
 F  P  P  G  H  F  K  D  P  K  R  L  Y  C  K  N  G  G  F  F ctgcgcatccaccccgacggccgagttgacggggtccgggagaagagcgaccctcacatc
 L  R  I  H  P  D  G  R  V  D  G  V  R  E  K  S  D  P  H  I aagctacaacttatagcagaagagagaggagttgtgtctatcaaggagtgtgtgctaac
 K  L  Q  L  I  A  E  E  R  G  V  V  S  I  K  G  V  C  A  N cgttacctggctatgaaggaagatggaagattactggcttctaaaagtgttacggatgag
 R  Y  L  A  M  K  E  D  G  R  L  L  A  S  K  S  V  T  D  E tgtttctttttgaacgattggaatctaatggctacaatacttaccggtcaaggaaatac
 C  F  F  F  E  R  L  E  S  N  G  Y  N  T  Y  R  S  R  K  Y accagttggtatgtggcactgaaacgaactgggcagtataaacttggatccaaaacagga
 T  S  W  Y  V  A  L  K  R  T  G  Q  Y  K  L  G  S  K  T  G cctgggcagaaagctatacttttcttccaatgtctgctaagagctga (SEQ ID NO: 7)
 P  G  Q  K  A  I  L  F  L  P  M  S  A  K  S  - (SEQ ID NO: 8)

(3) FGF2-QNCCm: Q65I, N111G, C78S, C96S
atggcagccgggagcatcaccacgctgcccgccttgcccgaggatggcggcagcggcgcc
 M  A  A  G  S  I  T  T  L  P  A  L  P  E  D  G  G  S  G  A ttcccgcccggccacttcaaggaccccaagcggctgtactgcaaaaacgggggcttcttc
 F  P  P  G  H  F  K  D  P  K  R  L  Y  C  K  N  G  G  F  F ctgcgcatccaccccgacggccgagttgacggggtccgggagaagagcgaccctcacatc
 L  R  I  H  P  D  G  R  V  D  G  V  R  E  K  S  D  P  H  I aagctacaacttatagcagaagagagaggagttgtgtctatcaaggagtagtgctaac
 K  L  Q  L  I  A  E  E  R  G  V  V  S  I  K  G  V  S  A  N cgttacctggctatgaaggaagatggaagattactggcttctaaaagtgttacggatgag
 R  Y  L  A  M  K  E  D  G  R  L  L  A  S  K  S  V  T  D  E tgtttctttttgaacgattggaatctaatggctacaatacttaccggtcaaggaaatac
 C  F  F  F  E  R  L  E  S  N  G  Y  N  T  Y  R  S  R  K  Y accagttggtatgtggcactgaaacgaactgggcagtataaacttggatccaaaacagga
 T  S  W  Y  V  A  L  K  R  T  G  Q  Y  K  L  G  S  K  T  G cctgggcagaaagctatacttttcttccaatgtctgctaagagctga (SEQ ID NO: 9)
 P  G  Q  K  A  I  L  F  L  P  M  S  A  K  S  - (SEQ ID NO: 10)

Figure 6:
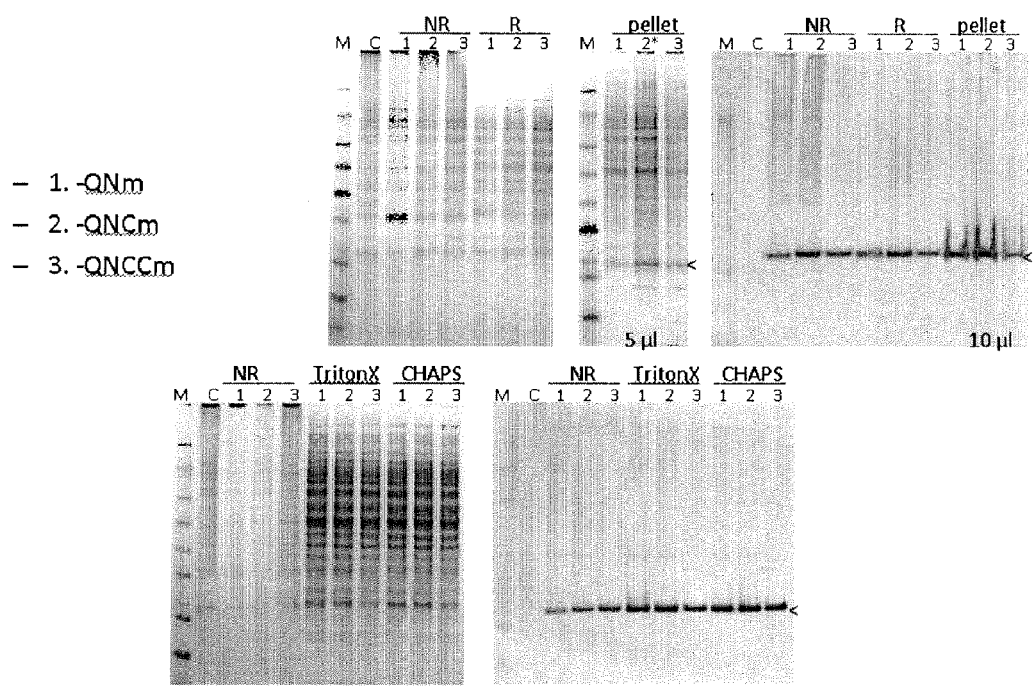
FIG. 6: Expression analysis of three engineered FGF2 from human cells.

Human cells were prepared and transfected as described in PCT/US2009/036975, which is incorporated herein by reference. The cells were adapted to a serum-free suspension culture and expression of the engineered molecules was analyzed by Coomassie-stained SDS-PAGE and western blotting. Results are shown in FIG. 6.

Expression levels of QNCm were approximately two-fold higher than that of QNm and QNCCm, and were nearly wild-type in both the supernatant and the detergent-washed pellet. This result is unexpected because substitution of the corresponding mutant amino acids of FGF1 to FGF2 did not result in an increased expression level.

Example 2

Purification

Figure 7:
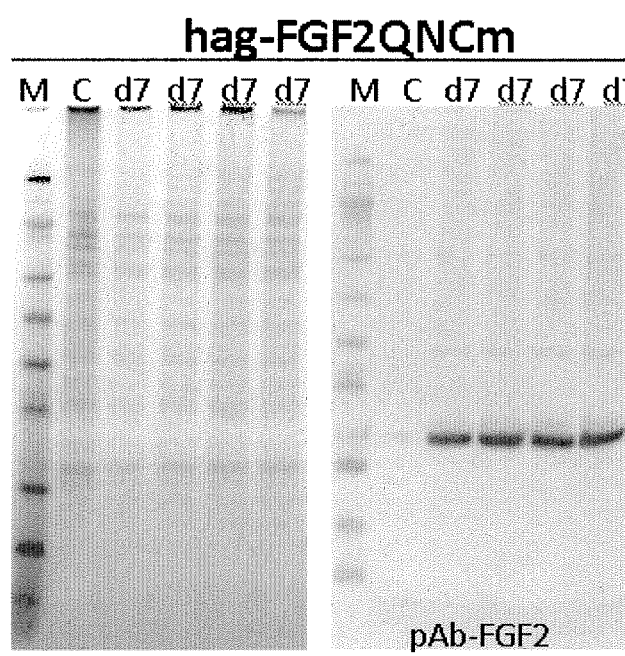
FIG. 7: QNCm FGF2 culture supernatant (left panel) and purified protein (right panel) visualized via SDS-PAGE Coomassie stain. Anti-FGF2 western blot of purified proteins (middle panel).

QNCm FGF2 was large cultured in serum-free media for 7 days and the conditioned medium was harvested for purification. Harvest culture medium was loaded on DEAE column equilibrated with 10 mM MES (pH 6.0) and FGF2 QNCm fraction was eluted with 10 mM MES (pH 6.0)/600 mM NaCl. FGF2 QNCm fraction from DEAE was next loaded on Heparin column equilibrated with 10 mM MES (pH 6.0) and purified FGF2 QNCm fraction was eluted with 10 mM MES (pH 6.0)/2.0 M NaCl. Culture supernatants and purified proteins were analyzed by western blot using a polyclonal antibody raised against FGF2 (FIG. 7).

Example 3

Cell-Based Assay for Thermo Stability

The stability and function of FGF2 variants was tested using a cell culture-based assay. Recombinant wild-type FGF2 purified from *E. coli* and FGF2 QNCm purified from human cells were placed at −80° C. for 24 hours, 37° C. for 2 hours, or 37° C. for 24 hours in serum-free culture medium. The proteins were then assayed for the capacity to promote 3T3 cell proliferation.

Briefly, 3T3 cells were resuspended in assay media containing 10% calf serum, and plated at a density of 5,000 cells/100 ml culture (passage 3). After overnight incubation, the media was twice changed to media containing 0.5% calf serum. FGF2 or FGF2 QNCm were added to the cultures at final concentrations of 1 ng/ml to 100 ng/ml and the cells were cultured for an additional 45 hours. Cell proliferation was measured by adding 20 µl of Promega Substrate Cell Titer 96 Aqueous One Solution Reagent to each well according to manufacturer instructions, and measuring the absorbance at 490 nm. The assay was performed in duplicate. Results are shown in FIG. 8.

Figure 8:
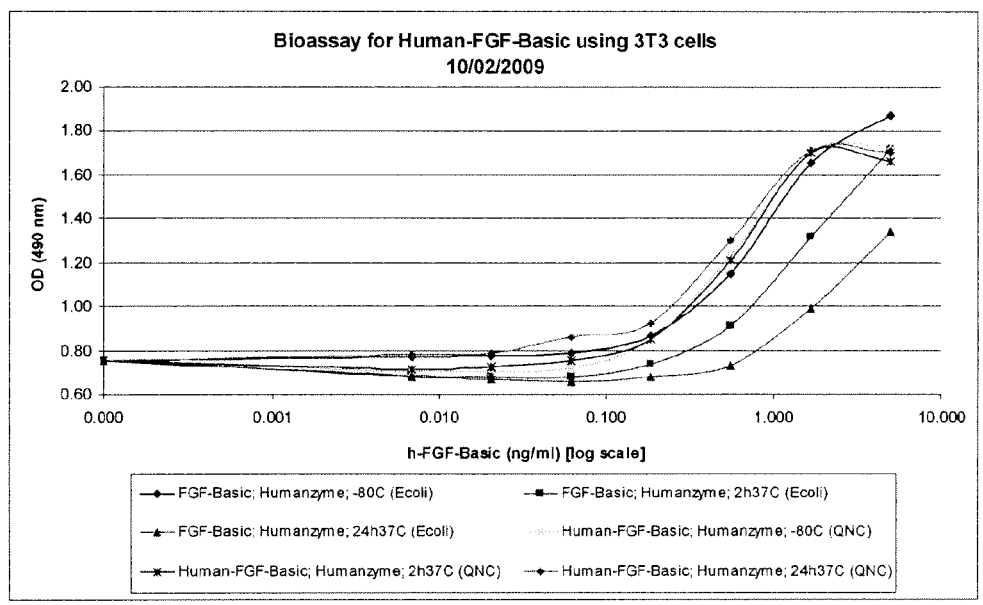
FIG. 8: FGF2 QNCm shows increased thermostability compared to wild-type FGF2 in a cell proliferation-based assay.
Figure 9:
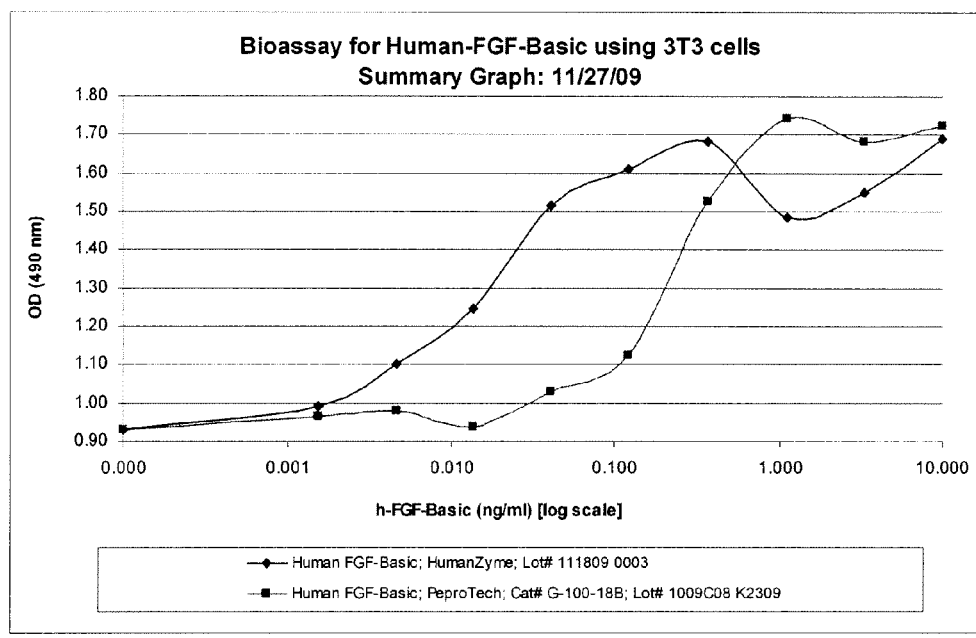
FIG. 9: FGF2 QNCm (represented by ●) shows increased activity compared to commercially available wild-type FGF2 (represented by ■) in a cell proliferation-based assay.

FGF2 QNCm showed comparable capacities to promote 3T3 cell proliferation after storage at −80° C., or pre-incubation at 37° C. for 2 or 24 hours (FIG. 8). By contrast, the activity of wild-type FGF2 was reduced to 50% and 10% of the wild-type by pre-incubation for 2 and 24 hours at 37° C., respectively. After two or 24 hours of pre-incubation at 37° C., FGF2 QNCm induced as much as 10-fold more cell proliferation than the wild-type protein, demonstrating that FGF2 QNCm has increased thermostability compared to the wild-type protein. FGF2 QNCm also showed increased thermostability compared to a commercially available wild-type FGF2 protein in the same assay (FIG. 9).

This example demonstrates that the methods and compositions of the present disclosure are useful for the culture of ES cells. The methods and compositions provide the technical advantages of reducing cost and labor in the culture of ES cells.

Example 4

Figure 10:
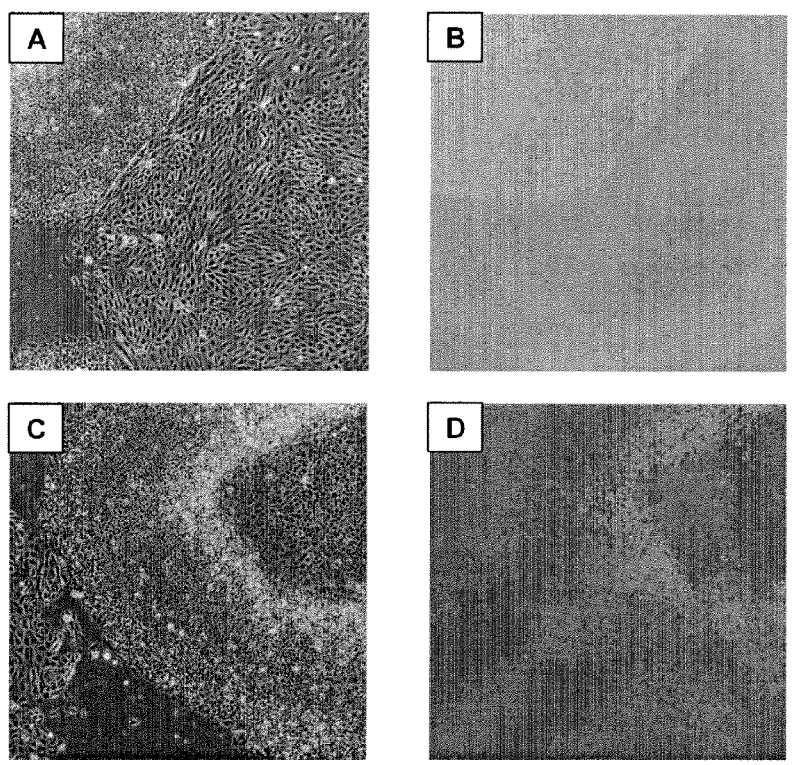
FIGS. 10(a)-(d): (a) Good looking human ES cell colony; (b) mCherry reporter to the Nanog promoter (a pluripotency related gene, i.e. stem cell gene). The loss or down regulation of Nanog is found in the differentiated cells; (c) differentiated stem cell colony showing the "donut"; (d) mCerry stain of C.

Engineered QNCm FGF2 Application to Human Embryonic Stem Cell Proliferation in Feeder-Independent Culture Human embryonic stem cells HUES-6 were feeder independently cultured in mTeSR1 media prepared according to the protocol of Ludwig T E et al. (2006) Nature Methods 3:637. FGF2 was added to 25% the recommended amount, with FGF2 supplementation every 48 hrs rather than every 24 hours as recommended. mTeSR1 is published human pluripotent stem cell culture media that is also sold commercially by Stem Cell Technologies. Reduction of the level and frequency of FGF2 supplementation promoted differentiation and death of the cells, as measured using the mCherry Nanog reporter (FIG. 10). These conditions promote a characteristic loss of stem cells in the central region of the colonies (so called the "donut" effect; FIG. 10C, 10D), not seen in proliferating cells (FIG. 10A, 10B). By contrast, cells supplemented with FGF2QNCm according to the same protocol showed fewer "donut" colonies (Table 1).

TABLE 1

| Cell Differentiation and Death in HUES-6 with Reduced FGF2 Supplementation | |
|---|---|
| | Differentiated colony numbers (average) |
| 25% wild-type FGF2 supplement | 14 |
| 25% QNCm FGF2 supplement | 5 |

These results demonstrate that FGF2QNCm has an increased capacity to maintain stem cells in an undifferentiated state compared to the wild-type protein. This example demonstrates that the methods and compositions of the present disclosure are useful for maintaining ES cells in an undifferentiated state in culture.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claimed is:

1. An isolated polypeptide variant of SEQ ID NO:2, comprising amino acid substitutions at positions Q65 and N111, wherein the amino acid substitution at position Q65 is selected from the group consisting of Q65L, Q65I, and Q65V, and wherein the amino acid substitution at position N111 is selected from the group consisting of N111A and N111G.

2. The isolated polypeptide of claim 1, wherein the polypeptide comprises amino acid substitutions Q65I, N111G, and C96S.

3. The isolated polypeptide of claim 2, wherein the polypeptide consists of the amino acid sequence set forth in SEQ ID NO: 8.

4. The isolated polypeptide of claim 2, wherein the polypeptide further comprises the amino acid substitution C78S.

5. The isolated polypeptide of claim 1, wherein the polypeptide further comprises an amino acid substitution selected from the group consisting of C96S and C96T.

6. The isolated polypeptide of claim 1, wherein the polypeptide comprises SEQ ID NO:6.

7. The isolated polypeptide of claim 1, wherein the polypeptide consists of the amino acid sequence set forth in SEQ ID NO:10.

8. A method for culturing human embryonic stem cells to maintain an undifferentiated morphology comprising culturing the embryonic stem cells in a feeder-independent culture medium comprising the polypeptide of claim 1.

9. The method of claim 8, wherein the feeder-independent medium is hESF9 or mTeSR1.

10. The method of claim 8, wherein the concentration of polypeptide is about 1.0 ng/µl to about 100 ng/µl of culture medium.

11. The method of claim 8, wherein the embryonic stems cells are human ES cells, mouse ES cells, bovine ES cells, or feline ES cells.

12. A composition comprising the polypeptide set forth in SEQ ID NO:8 and a feeder-independent media for human embryonic stem cell culture.

13. A composition comprising the polypeptide set forth in SEQ ID NO:10 and a feeder-independent media for human embryonic stem cell culture.

* * * * *